(12) United States Patent
Canon

(10) Patent No.: US 11,534,116 B1
(45) Date of Patent: Dec. 27, 2022

(54) SURGICAL OR EXAM TABLE THAT FACILITATES IMAGING DURING PROCEDURES

(71) Applicant: William Barry Canon, College Station, TX (US)

(72) Inventor: William Barry Canon, College Station, TX (US)

( * ) Notice: Subject to any disclaimer, the term of this patent is extended or adjusted under 35 U.S.C. 154(b) by 0 days.

(21) Appl. No.: 17/576,777

(22) Filed: Jan. 14, 2022

Related U.S. Application Data

(60) Provisional application No. 63/141,337, filed on Jan. 25, 2021.

(51) Int. Cl.
| | |
|---|---|
| *A61G 13/06* | (2006.01) |
| *A61B 6/04* | (2006.01) |
| *A61G 13/10* | (2006.01) |

(52) U.S. Cl.
CPC ............ *A61B 6/0407* (2013.01); *A61G 13/06* (2013.01); *A61G 13/10* (2013.01)

(58) Field of Classification Search
CPC ....... A61B 6/0407; A61G 13/06; A61G 13/10
See application file for complete search history.

(56) References Cited

U.S. PATENT DOCUMENTS 6,163,902 A * 12/2000 Mollette .............. A61B 6/0421
5/601
7,913,337 B1 * 3/2011 Masson ................ A61G 1/0287
5/942

* cited by examiner

*Primary Examiner* — Fredrick C Conley
(74) *Attorney, Agent, or Firm* — Plager Schack LLP; Mark H. Plager; Naomi Mann

(57) ABSTRACT

A surgical or exam table includes a radiolucent patient support surface; and a shelf beneath the patient support surface, wherein an x-ray panel may be supported on said shelf for x-raying a human or animal subject resting on the support surface.

12 Claims, 3 Drawing Sheets

SURGICAL OR EXAM TABLE THAT FACILITATES IMAGING DURING PROCEDURES

RELATED APPLICATION

This application claims benefit to U.S. Provisional Application No. 63/141,337 filed Jan. 25, 2021, which is incorporated by reference herein in its entirety.

BACKGROUND

The embodiments herein relate generally to devices and methods for performing medical procedures.

X-raying a human or animal subject may be critical to medical treatment. However, movement of the subject might be inconvenient or even harmful during regular or emergency procedures, such as examinations and surgeries. Additionally, some facilities, such as veterinary and small clinics, may be ill equipped for whole body scanning. As such, an improved system is desirable.

SUMMARY

According to various embodiments, disclosed is a surgical or exam table, comprising a radiolucent or x-ray transparent support surface configured to support a patient, which enables placement of any x-ray detector panel underneath the support surface. In embodiments, the medical table may comprise a support member coupled to the x-ray transparent support surface, which supports the x-ray transparent support surface above a ground level. In certain embodiments, the table may further comprise a shelf connected underneath the support surface, which supports the x-ray detector panel.

According to various embodiments, further disclosed is an x-ray imaging method comprising: providing an x-ray transparent support surface, the x-ray transparent patient support surface being elevated above a ground level and configured to support a patient; placing a patient on top of the x-ray transparent support surface; placing an x-ray detector member on a detector support member beneath the x-ray transparent support surface; and taking an x-ray of the patient by radiating x-rays through the patient and x-ray transparent support surface to expose the x-ray detector member beneath the x-ray transparent support surface.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
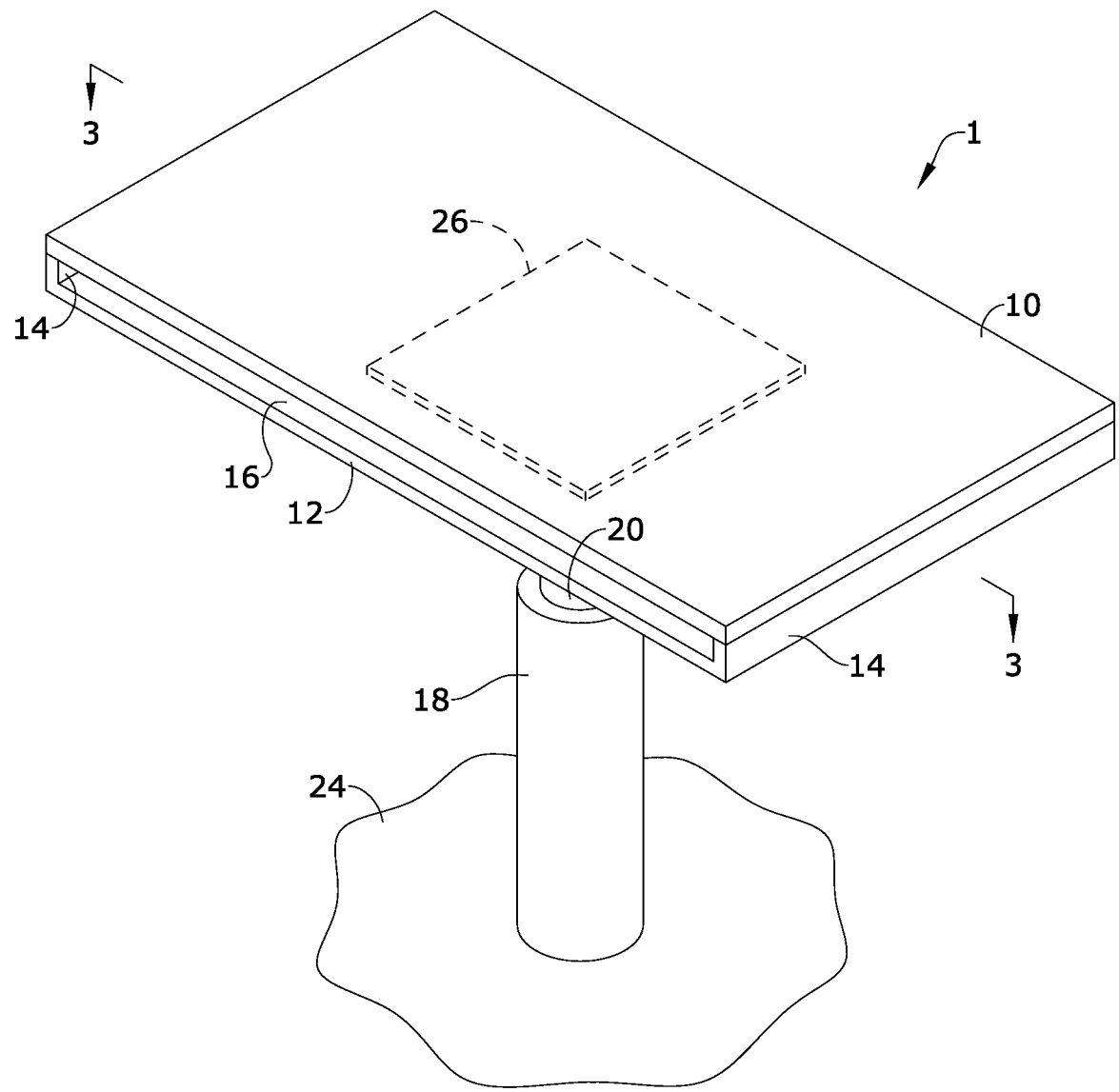
FIG. 1 is a perspective view of a medical table, in accordance with various embodiments.
Figure 2:
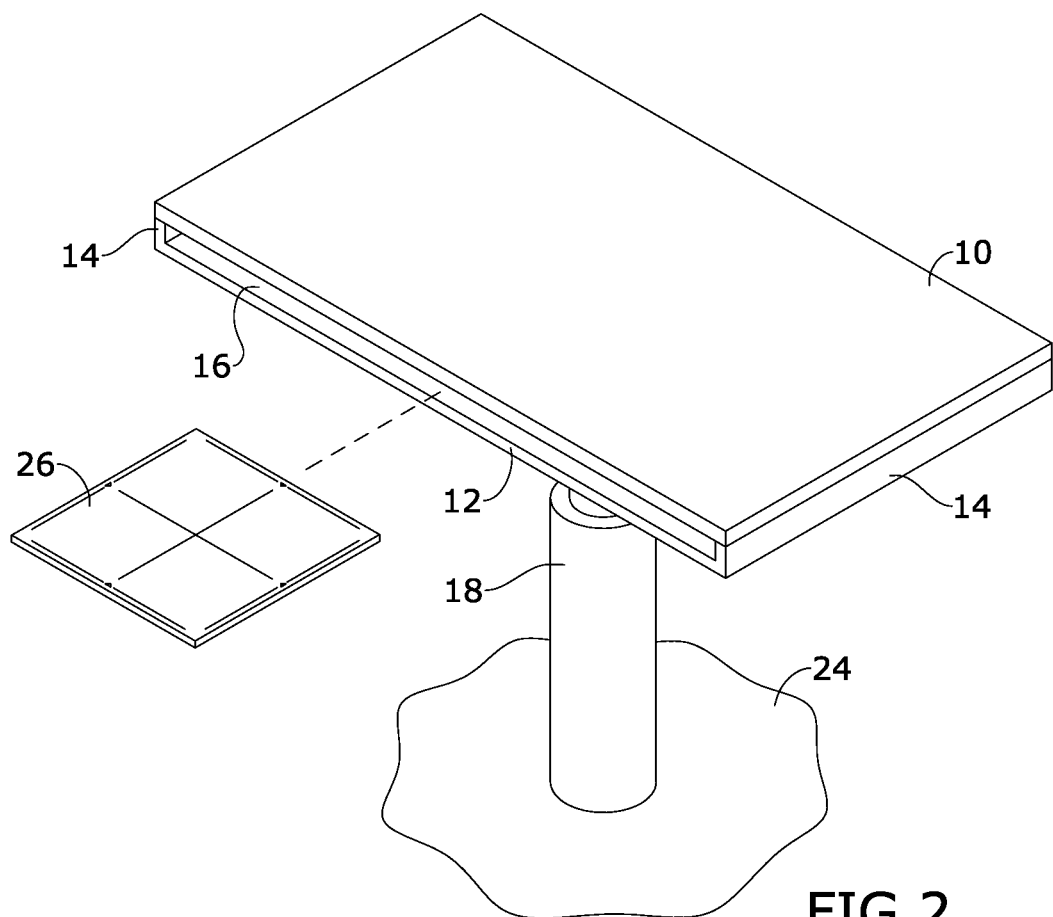
FIG. 2 is a perspective view of the medical table, showing insertion of an x-ray panel.
Figure 3:
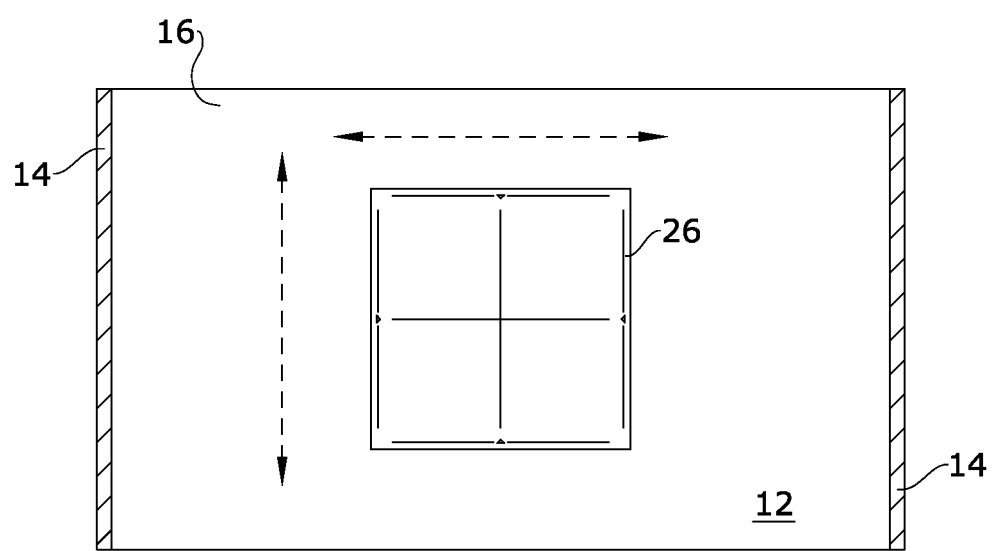
FIG. 3 is a sectional view of the medical table, taken along line 3-3 in FIG. 1, and illustrating movement of the x-ray panel to multiple positions.

In the following detailed description of the invention, numerous details, examples, and embodiments of the invention are described. However, it will be clear and apparent to one skilled in the art that the invention is not limited to the embodiments set forth and that the invention can be adapted for any of several applications.

Medical procedures, including emergency and routine examinations, surgeries, and the like may utilize a c-arm x-ray device, if available, to provide imaging. In some cases, practitioners may slide an x-ray detector panel under a patient in order to obtain an x-ray image. This may require moving or repositioning the patient, which may be difficult for both the practitioner and patient and may risk injury to the patient in some cases.

The disclosed subject matter provides a system comprising a medical table 1 incorporating a radiolucent patient support surface which enables x-ray imaging of a patient supported directly on the table during a medical and/or examination procedure. In some embodiments, the disclosed system may utilize equipment which is readily available at the facility, such as an existing x-ray panel and portable x-ray source, with the disclosed medical table. The disclosed system may further enable a general exam and/or surgery table to function as an imaging table without requiring movement of the patient back and forth from a treatment/surgery location to a dedicated x-ray imaging location.

With reference to the accompanying figures, and in accordance with various embodiments, medical table 1 may comprise an x-ray transparent support surface 10 ("tabletop") configured to support a patient (human or animal). In embodiments, x-ray transparent support surface 10 may be made, for example, of carbon fiber, solid carbon fiber, and/or polycarbonate. In certain embodiments, the entire area of x-ray transparent support surface 10 may be x-ray transparent. However, in alternate embodiments, only a portion of the area of x-ray transparent support surface 10 may be x-ray transparent, wherein support surface 10 may comprise region(s) which are x-ray transparent and other region(s) which are not x-ray transparent. In further alternate embodiments, support surface 10 may comprise multiple regions or panels, which may be coupled to one another.

In certain embodiments, medical table 1 may be use as a surgical table and/or an examination table. x-ray transparent support surface 10 may support the patient on its upper surface, while an x-ray detector member 26 may be placed beneath its bottom surface. In embodiments, x-ray detector member 26 may be any type of x-ray detector panel or sensor, including but not limited to imaging detectors such as photographic plates and x-ray or photographic film, various digitizing devices such as image plates or flat panel detectors, and other devices currently available or which may become available with emerging technology. Thus, an x-ray of the patient may be taken while the patient rests on support surface 10, without requiring movement of the patient. The x-ray exam may be performed by radiating x-rays through the patient and x-ray transparent support surface 10 to expose x-ray detector member 26 beneath support surface 10. In some embodiments, x-rays may be fired using, for example, a hand-held and/or portable x-ray unit.

In embodiments, medical table 1 may include a detector support member 12 for support of x-ray detector member 26 beneath x-ray transparent support surface 10. In further embodiments, medical table 1 may include at least one support leg 18.

In certain embodiments, detector support member 12 may be a shelf provided directly below x-ray transparent support surface 10. In some embodiments, support member 12 may be an integral component of medical table 1. In some embodiments, support member 12 may span approximately the entire area of x-ray transparent support surface 10, thus allowing full movement of x-ray detector member 26 anywhere under x-ray transparent support surface 10. In certain embodiments, support member 12 may comprise a horizontal panel connected to x-ray transparent support surface 10 via vertical side panels 14 and may be space apart from x-ray transparent support surface 10 to form an opening 16 between x-ray transparent support surface 10, side panels 14, and support member 12, as shown in the figures. As such, x-ray detector member 26 may be inserted through opening 16 and supported on support member 12 below x-ray transparent support surface 10 for x-raying a patient resting on x-ray transparent support surface 10. In embodiments, opening 16 may be formed on opposite sides of medical table 1, such that x-ray detector member 26 may be inserted from either side of the table. It shall be appreciated that different devices/components may be used to provide a support surface for x-ray detector member 26 in alternate embodiments. For example, in some alternate embodiments, a support table that is lower than medical table 1, and which is an independent component from the medical table, may be used for supporting x-ray detector member 26 underneath x-ray transparent support surface 10. Such support table may include wheels to enable it to be maneuvered underneath support surface 10.

Figure 4:
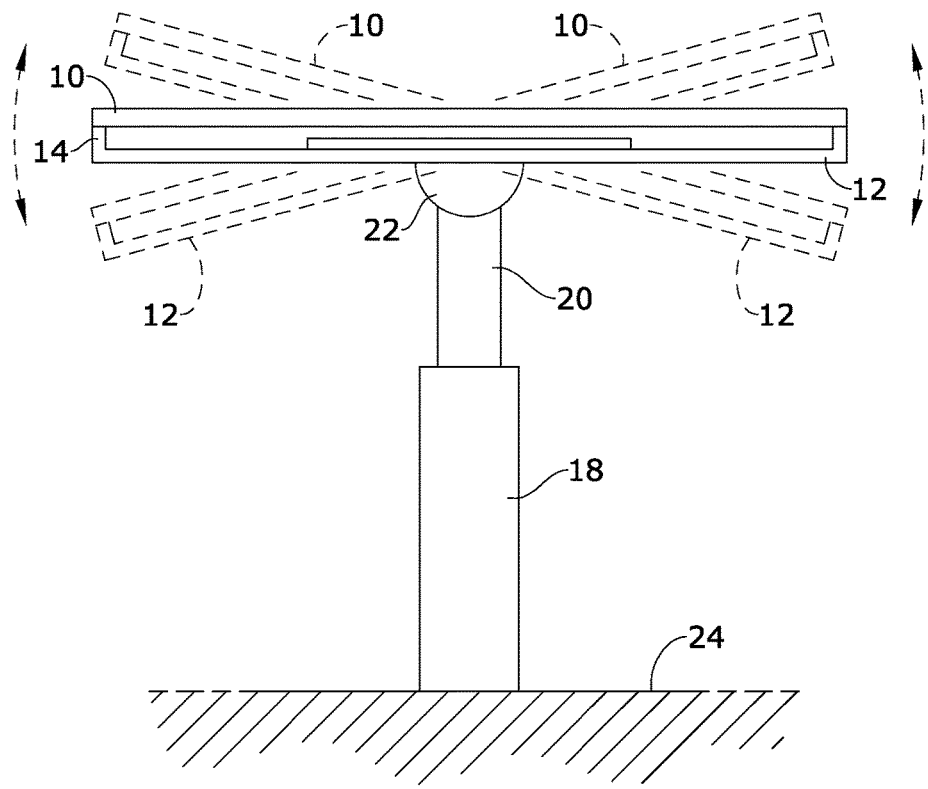
FIG. 4 is a front view of the medical table, illustrating a tilt adjustment feature of the table.
Figure 5:
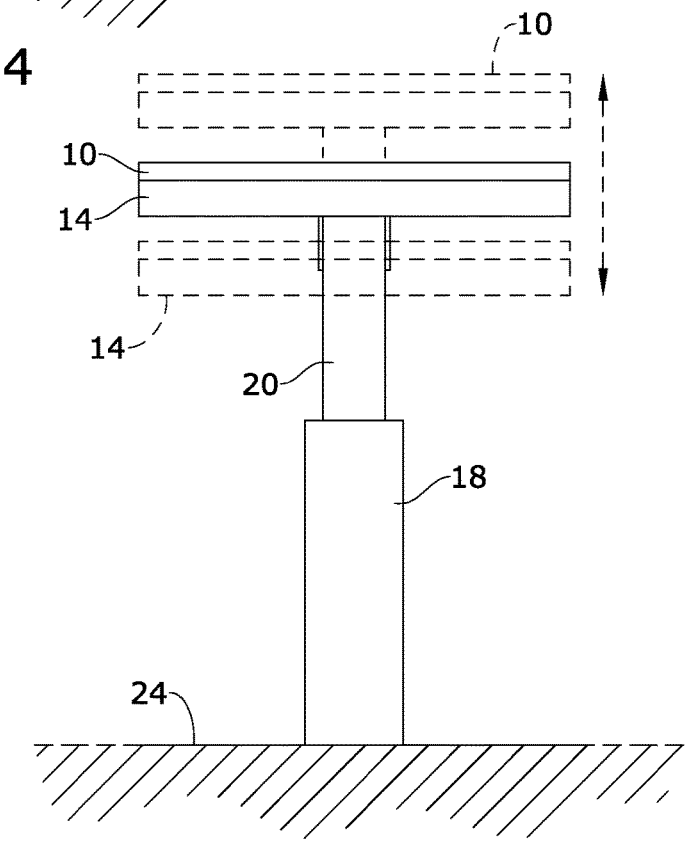
FIG. 5 is a front view of the medical table, illustrating a height adjustment feature of the table.

In embodiments, table support leg 18 may be configured to support x-ray transparent support surface 10 above a ground surface 24 (e.g., hospital floor). According to an exemplary embodiment, leg 18 may be coupled to a bottom side of the support member 12, which is integrally coupled to x-ray transparent support surface 10, as shown in the figures. In some embodiments, support leg 18 may be configured to allow x-ray transparent support surface 10 to pivot, and/or rotate (see FIG. 4) about one or more axes of rotation. To this end, leg 18 may be coupled to x-ray transparent support surface 10 via pivot joint 22. In some embodiments, support leg 18 may be height adjustable. For example, leg 18 may comprise an extension 20, which may telescope from leg 18 and is coupled to support surface 10. In one embodiment, extension 20 may extend from support leg 18 and may be coupled to pivot joint 22, and pivot joint 22 may be coupled to support member 12/support surface 10, wherein support leg 18 supports medical table 1 on surface 24. Thus, leg 18, extension 20, and pivot joint 22 may together form a pivoting pedestal mount of medical table 1 which enables medical table 1 to tilt, roll, swivel, and be height adjusted. In this manner, the position of a patient supported on medical table 1 may be adjusted to a suitable working height and angle for the practitioner, for easily taking an x-ray, and for comfort of the patient. In some embodiments, leg 18 may be removable from x-ray transparent support surface 10/support member 12 for easy transport and relocation.

In some embodiments, medical table 1 may further comprise one or more fluid-draining channels, which may be coupled to one or more side edges of support surface 10. In embodiments, medical table 1 may comprise up to four fluid draining channels for a four-sided tabletop as depicted in the figures.

In further embodiments, x-ray transparent support surface 10 may comprise multiple sections which are rotationally coupled or hinged to one another. In certain embodiments, x-ray transparent support surface 10 may comprise two x-ray transparent sections which are hingedly coupled to one another, and may be positioned at an angle (e.g., up to approximately 45 degrees) with respect to one another to enable medical table 1 to recline. In one embodiment, a hinge coupling the two sections may be provided along an intermediate or approximate mid-point of the long axis of the table. This may facilitate imaging, particularly during surgery, where it may be particularly difficult to maneuver the patient and may provide more comfort to the patient. Additionally, the hinge function may enable medical table 1 to be folded up for transport (wherein leg 18 may be removed), which may be particularly useful for a mobile veterinary clinic, and/or small examination rooms. According to another embodiment, x-ray transparent support surface 10 may comprise multiple x-ray transparent sections which may be attachable and detachable to one another for compact storage and/or easy transport of the table.

It shall be appreciated that the components of medical table 1 described in several embodiments herein may comprise any alternative known materials in the field and be of any size and/or dimensions. It shall be appreciated that the components of medical table 1 described herein may be manufactured and assembled using any known techniques in the field. In one example, medical table 1 may be constructed by shaping support member 12 and side panels 14 from a single sheet of aluminum or stainless steel using a brake press that forms the side panels. A carbon fiber or polycarbonate top may be fitted precisely within the side panels and attached via screws that insert through holes provided within support surface 10 and the top sides of side panels 14. Support member 12 may be fitted with a small electric or manual pivot component around the middle of the support member. Such pivot component may be coupled to a motorized pedestal or telescoping leg. The pivot component may be coupled to support member 12 by welding and to leg 18 via bolts, for example. This assembly provides a medical table which may be easily disassembled for shipping or relocation.

It shall be appreciated that the disclosed medical table 1 can have multiple configurations in different embodiments. It shall be appreciated that medical table 1 may have various support structures, including any number of legs, or no legs in alternate embodiments. For example, x-ray transparent support surface 10 and support member 12 may be used without the table support leg 18 and may be connected to a wall of a clinic or mobile medical van or supported directly on a floor. In embodiments, x-ray transparent support surface 10 and support member 12 may be attached by hinge support to the wall and held steady underneath by a metal rod while in use.

In embodiments, the disclosed subject matter may be particularly useful to the veterinary industry, as well as the medical industry. The disclosed subject matter can additionally be used in other applications, for convenient x-ray examination of any component that needs x-ray analysis. This may include non-destructive testing of drilled cores or machine parts, cadaver imaging or autopsies, and the like.

The disclosed medical table may be used for surgery and examination of a human or animal subject, whereby the x-ray detector member or detector panel can be moved, unhindered, under the entire length/body of the subject. In some embodiments, the disclosed apparatus and method enables total patient x-ray imaging without moving the patient (or anything attached to the patient such as IV tubes, monitor cables or anesthesia equipment).

The disclosed subject matter may also provide a low-cost alternative for whole body imaging during routine exam and surgery. It allows x-rays to be performed using common x-ray panels which may be available in small facilities, and may replace expensive, bulky equipment such as radiographic c-arms.

The constituent elements of the disclosed device and system listed herein are intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device. Terms such as 'approximate,' 'approximately,' 'about,' etc., as used herein indicate a deviation of within +/−10%. Relationships between the various elements of the disclosed device as described herein are presented as illustrative examples only, and not intended to limit the scope or nature of the relationships between the various elements. Persons of ordinary skill in the art may appreciate that numerous design configurations may be possible to enjoy the functional benefits of the inventive systems. Thus, given the wide variety of configurations and arrangements of embodiments of the present invention, the scope of the invention is reflected by the breadth of the claims below rather than narrowed by the embodiments described above.

What is claimed is:

1. An x-ray imaging method comprising:
   providing an elevated x-ray transparent support surface configured to support a patient;
   placing a patient on top of the x-ray transparent support surface;
   placing an x-ray detector member on a detector support member beneath the elevated x-ray transparent support surface; and
   taking an x-ray of the patient by radiating x-rays through the patient and x-ray transparent support surface to expose the x-ray detector member beneath the x-ray transparent support surface,
   wherein the detector support member comprises a horizontal panel connected to the x-ray transparent support surface via a pair of vertical side panels,
   wherein the detector support member is space apart from the x-ray transparent support surface to form an unobstructed opening between the x-ray transparent support surface, the pair of vertical side panels, and the detector support member, said unobstructed opening extending along an entire length of the x-ray transparent support surface,
   wherein the x-ray detector member can be inserted through said opening and supported on the detector support member such that the x-ray detector member is allowed full movement anywhere under x-ray transparent support surface,
   wherein the x-ray transparent support surface is supported on at least one support leg, and
   wherein the x-ray transparent support surface can be tilted, swiveled, rolled, and/or height adjusted with respect to the support leg.

2. The x-ray imaging method of claim 1, wherein the patient is a human or animal.

3. The x-ray imaging method of claim 1, wherein the x-ray transparent support surface is a component of a medical table used for surgery and/or examination of the patient.

4. The x-ray imaging method of claim 1, wherein the method is used for treatment of animals.

5. The x-ray imaging method of claim 1, wherein the x-ray transparent support surface comprises multiple parts which can be repositioned with respect to one another and/or disconnected from one another.

6. The x-ray imaging method of claim 1, wherein the x-ray transparent support surface is supported on a single support leg which is approximately centered about the x-ray transparent support surface.

7. The x-ray imaging method of claim 1, wherein the x-ray transparent support surface is made of carbon fiber.

8. A medical table comprising:
   an x-ray transparent support surface configured to support a patient;
   at least one support leg, which supports the x-ray transparent support surface above a ground level,
   a detector support member coupled to the x-ray transparent support member and providing a shelf beneath the x-ray transparent support member configured to hold an x-ray detector member, entire length of table
   wherein the detector support member comprises a horizontal panel connected to the x-ray transparent support surface via a pair of vertical side panels,
   wherein the detector support member is space apart from the x-ray transparent support surface to form an unobstructed opening between the x-ray transparent support surface, the pair of vertical side panels, and the detector support member, said unobstructed opening extending along an entire length of the x-ray transparent support surface,
   wherein the x-ray detector member can be inserted through said opening and supported on the detector support member such that the x-ray detector member is allowed full movement anywhere under x-ray transparent support surface, and
   wherein the x-ray transparent support surface can be tilted, swiveled, rolled, and/or height adjusted with respect to the support leg.

9. The medical table of claim 8, wherein the x-ray transparent support surface is supported on a single leg which is approximately centered about the x-ray transparent support surface, and is coupled to the x-ray transparent support surface via a pivot joint.

10. The medical table of claim 9, wherein the support leg is height adjustable.

11. The medical table of claim 8, wherein the medical table is a veterinary table used for the treatment of animals.

12. The medical table of claim 8, wherein the x-ray transparent support surface is made of carbon fiber.

* * * * *